(12) United States Patent
Hoppe et al.

(10) Patent No.: US 6,251,446 B1
(45) Date of Patent: Jun. 26, 2001

(54) USE OF XANTHOMONAS LIQUID CARBOHYDRATE FERMENTATION PRODUCT IN FOODS

(75) Inventors: Craig Alan Hoppe, Plainsboro; Jeanette Lawrence, Dayton; Amr Shaheed, Manalapan, all of NJ (US)

(73) Assignee: Rhodia Inc., Cransbury, NJ (US)

( * ) Notice: Subject to any disclaimer, the term of this patent is extended or adjusted under 35 U.S.C. 154(b) by 0 days.

(21) Appl. No.: 09/550,130

(22) Filed: Apr. 17, 2000

Related U.S. Application Data

(63) Continuation-in-part of application No. 08/971,067, filed on Nov. 14, 1997, now abandoned.

(51) Int. Cl.[7] .................................................. C12P 19/06
(52) U.S. Cl. ............................................ 426/48; 435/104
(58) Field of Search .................................. 435/104, 910; 426/48, 573; 536/60, 52, 114, 127, 123

(56) References Cited

U.S. PATENT DOCUMENTS

| | | | | |
|---|---|---|---|---|
| 3,659,026 | * | 4/1972 | Schuppner | 424/361 |
| 4,299,825 | * | 11/1981 | Lee | 424/180 |
| 4,399,160 | * | 8/1983 | Schwartz et al. | 426/41 |
| 4,442,128 | * | 4/1984 | Schwartz et al. | 426/41 |
| 4,444,792 | * | 4/1984 | Schwartz et al. | 426/41 |
| 4,485,020 | * | 11/1984 | Shay et al. | 252/8.55 |
| 4,743,452 | * | 5/1988 | Felske et al. | 426/19 |
| 4,794,015 | * | 12/1988 | Fujita et al. | 426/589 |
| 4,888,190 | * | 12/1989 | Hashimoto et al. | 426/231 |
| 5,035,903 | * | 7/1991 | Silva | 426/19 |
| 5,118,626 | * | 6/1992 | Hashimoto et al. | 435/289 |
| 5,480,785 | * | 1/1996 | de Troomstembergh et al. | 435/104 |

FOREIGN PATENT DOCUMENTS 0 549 230 A2 * 12/1992 (EP) .............................. C12P/19/06

OTHER PUBLICATIONS

Mixed Polysaccharide Gels Formed Between Xanthan Gum and Glucomannan, P.A. Williams, P. Annable, G.O. Phillips and K. Nishinari, Food Hydrocolloids: Structures, Properties and Functions, Plenum Press, New York, 1994, pp. 435–449.*

* cited by examiner

Primary Examiner—Keith Hendricks
(74) Attorney, Agent, or Firm—Kevin E. McVeigh

(57) ABSTRACT

A food or pharmaceutical composition including a liquid composition comprising the liquid fermentation broth product of a biologically active substance, in a carbohydrate medium other than dairy whey wherein said liquid fermentation broth product has not been subject to any concentrating or drying steps prior to introduction of the broth product into said food or pharmaceutical composition is provided.

7 Claims, 3 Drawing Sheets

USE OF XANTHOMONAS LIQUID CARBOHYDRATE FERMENTATION PRODUCT IN FOODS

RELATED APPLICATION

This application is a continuation-in-part of application Ser. No. 08/971,067, filed Nov. 14, 1997, now abandoned.

BACKGROUND OF THE INVENTION

1. Field of the Invention

The present invention relates to carbohydrate fermentation products which may be used in food or pharmaceutical applications and requires minimal processing steps. More specifically, the invention comprises the use of a xanthan gum broth in liquid food or pharmaceutical compositions wherein the broth medium is a carbohydrate other than whey and wherein the broth is used directly without the need for filtration and purification processing steps.

2. Technology Description

Carbohydrate fermentation products, such as xanthan gum, are commonly used as additives, such as thickening agents for food and pharmaceutical ingredients. The fermentation of carbohydrates to produce biosynthetic water-soluble gums by the action of Xanthomonas bacteria is well known. The earliest work in this field was conducted by the U.S. Department of Agriculture and is described in U.S. Pat. No. 3,000,790. Particularly well known is the action of *Xanthomonas campestris* NRRL B-1459 on a glucose substrate.

Xanthomonas hydrophilic colloid (i.e., xanthan gum) is produced by transferring *Xanthomonas campestris* bacteria to a suitable medium and conditioning it to growth through two steps before allowing it to grow in a final medium containing 3 percent glucose. After 96 hours at 30° C. with suitable aeration and stirring, Xanthomonas hydrophilic colloid is produced in approximately 1% concentration. Modified fermentation processes are described in U.S. Pat. Nos. 3,391,060; 3,391,061; 3,427,226; 3,455,786; 3,565,763; and the like.

Xanthomonas hydrophilic colloid is a microbial heteropolysaccharide which contains mannose, glucose, glucuronic acid, O-acetyl radicals and acetal-linked pyruvic acid in a molar ratio of 2:2:1:1:0.5.

While *Xanthomonas campestris* is the bacteria of choice for the purpose of producing the biosynthetic Xanthomonas hydrophilic colloid, other Xanthomonas species may be employed such as *X. begoniae, X. malvacearum, X. carotae, X. incanae, X. phaseoli, X. vesicatoria, X. papavericola, X. translucens, X. vasculorum,* and *X. hedrae.*

In practice when xanthan gum is typically used as a thickening agent in a food or pharmaceutical composition, the fermentation broth is typically subject to processing conditions such as drying, centrifuging and the like to yield a purified powder. For example, In a typical process for clarification of a Xanthomonas fermentation broth and/or recovery of the Xanthomonas hydrocolloid component, the broth is diluted with water to reduce its viscosity, and optionally the diluted broth is centrifuged or filtered to remove suspended insoluble solids. A salt such as potassium chloride and a nonsolvent such as methanol or isopropanol are added to the broth to flocculate the gum in the, potassium form, which gum is then recovered by centrifugation or other solid/liquid separation technique. Further dissolution, reprecipitating and washing steps are usually employed. To yield xanthan gum powder, additional "downstream" processing steps such as drying, milling, sieving and packaging for customer use. There are significant costs involved in such steps and it would be desirable to omit these steps for economic reasons.

In addition, while the xanthan gum powder compositions typically are capable of thickening liquid food compositions, additional improvements in viscosity performance would be desired in homogenized foods such as salad dressings.

U.S. Pat. No. 4,299,825 suggests a process for clarifying and concentrating Xanthomonas heteropolysaccharide fermentation broth, which process includes filtration and ultrafiltration steps. The resulting clarified and concentrated material is suggested for use in foodstuffs, drugs and cosmetics, as well as a thickening agent for oil recovery operations. Despite the advances suggested in the patent, the filtration and ultrafiltration steps add significant processing costs to the manufacturer.

U.S. Pat. Nos. 4,442,128 and 4,444,792 suggests the fermentation of an organism such as *Xanthomonas campestris* in a dairy whey environment to yield a whey product containing a thickening polymer that serves as a thickening agent. The reference fails to suggest that other carbohydrate sources can be used as the fermentation medium.

Despite the above teachings, there still exists a need in the art for a carbohydrate fermentation product which can be produced using a minimum amount of unit processing steps and used directly in food or pharmaceutical applications.

There exists yet another need in the art for a thickening agent which demonstrates superior thickening properties in homogenized liquid foods, such as salad dressings.

BRIEF SUMMARY OF THE INVENTION

In accordance with the present invention a food or pharmaceutical composition containing a food or pharmaceutical ingredient and a liquid Xanthomonas hydrocolloid thickening agent which is a carbohydrate fermentation liquid broth product which is produced using a minimum amount of unit processing steps and used directly in food or pharmaceutical applications is provided. More specifically, the invention comprises a food or pharmaceutical composition including a liquid composition comprising the food or pharmaceutical ingredient and the liquid fermentation broth product of a biologically active substance, preferably xanthan gum in a carbohydrate medium other than dairy whey wherein said liquid fermentation broth product has not been subject to any concentrating or drying steps prior to introduction into said food or pharmaceutical composition.

In preferred embodiments of the present invention, the carbohydrate medium is either glucose or hydrolyzed starch.

Another embodiment of the present invention comprises a homogenized liquid food or pharmaceutical composition including a thickening agent comprising the liquid fermentation broth product of Xanthomonas in a carbohydrate medium other than dairy whey wherein said liquid fermentation broth product has not been subject to any concentrating or drying steps prior to introduction into said food or pharmaceutical composition.

In preferred embodiments, the homogenized liquid food or pharmaceutical composition comprises a salad dressing, sauce, beverage or condiment.

Still another embodiment of the present invention comprises a method for making a food or pharmaceutical composition comprising the steps of:

(a) producing a food-grade biopolymer by fermentation in a carbohydrate medium other than dairy whey to yield a liquid fermentation broth product; and (b) directly adding said liquid fermentation broth product to food or pharmaceutical ingredients to yield a food or pharmaceutical composition.

In preferred embodiments of the present invention, the carbohydrate medium can be treated with acid prior to or during fermentation.

An object of the present invention is to provide a food or pharmaceutical composition which includes a liquid composition comprising the liquid fermentation broth product of Xanthomonas in a carbohydrate medium other than dairy whey wherein said liquid fermentation broth product has not been subject to any concentrating or drying steps prior to introduction into said food or pharmaceutical composition.

Still another object of the present invention is to provide a homogenized food product having improved viscosity properties.

A further object of the present invention is to provide a cost efficient process for producing foods which include the liquid fermentation broth product of biopolymers.

These, and other objects, will readily be apparent to those skilled in the art as reference is made to the drawings and detailed description of the preferred embodiment.

DETAILED DESCRIPTION OF THE PREFERRED EMBODIMENT

Figure 1:
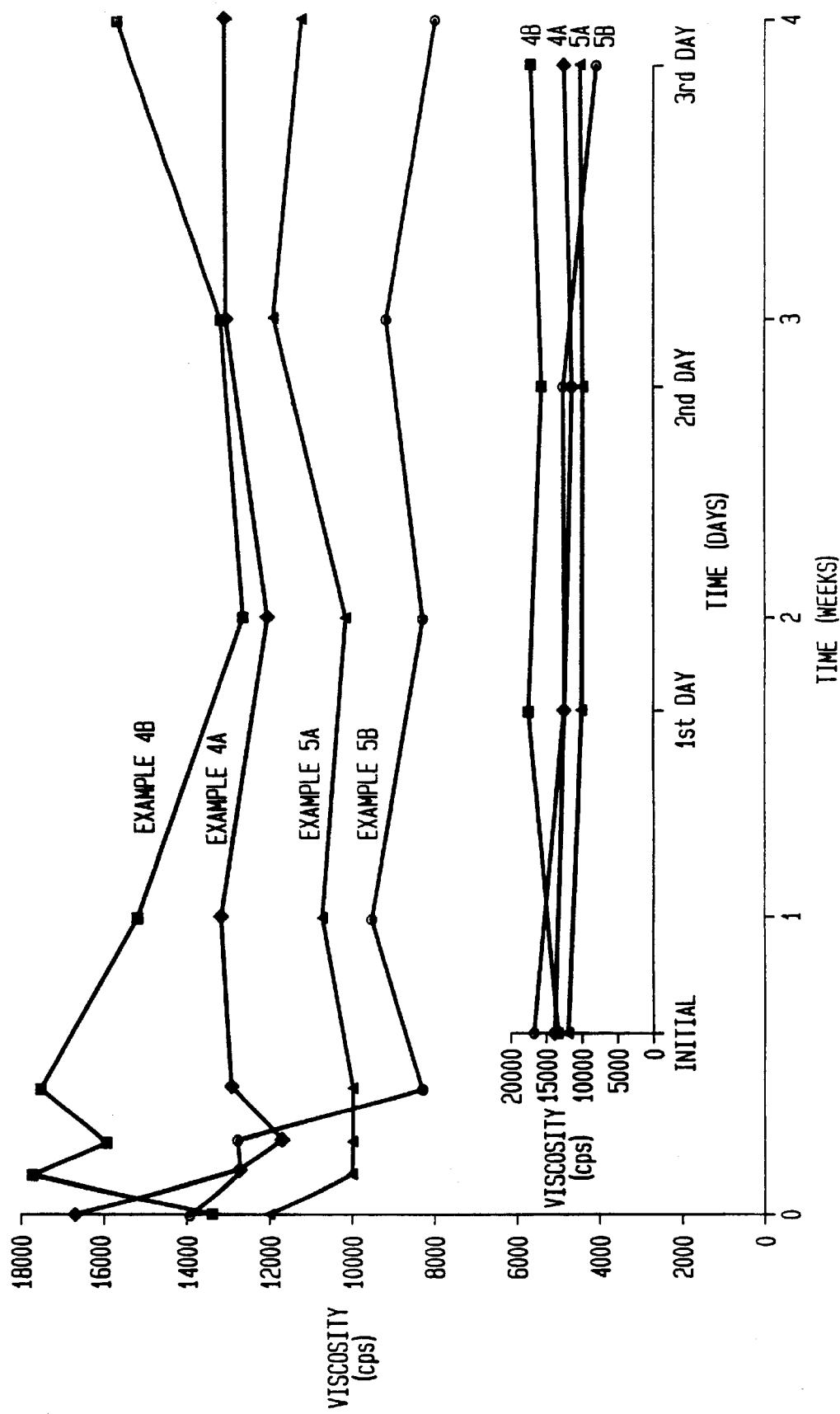
FIGS. 1 and 2 are viscosity graphs for the Compositions of Examples 4 and 5.

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention provides for an economical way to utilize biopolymer liquid fermentation broth products in food or pharmaceutical applications. In practice, the production of food grade fermentation products, such as xanthan gum powder, are produced by a sequence of process steps. Such steps typically include, in sequence, the following: strain selection, fermentation in a carbohydrate medium, thermal treatment, precipitation, centrifugation, drying, milling, sieving and packaging. The inventors have surprisingly discovered that the post fermentation steps of precipitation, centrifugation, drying, milling, sieving and packaging may be omitted and a useful product obtained for liquid foodstuffs and pharmaceuticals with great costs savings to the end use manufacturer.

The first step of the inventive process involves the selection of the biologically active substance which through fermentation yields a biopolymer. The polymer is generically defined to include any and all which, after fermentation in a carbohydrate medium may have applications as additives in liquid food or pharmaceutical compositions. In preferred embodiments, the biopolymer selected is derived from the group of polymers formed from fermentation of the genus Xanthomonas. While *Xanthomonas campestris* is the biologically active substance of choice for the purpose of producing the biosynthetic Xanthomonas hydrophilic colloid, other Xanthomonas species may be employed such as *X. begoniae, X. malvacearum, X. carotae, X. incanae, X. phaseoli, X. vesicatoria, X. papavericola, X. translucens, X. vasculorum,* and *X. hedrae.*

In practice, the biologically active substance is fermented in a carbohydrate substrate other then dairy whey which may be either of the monosaccharide, disaccharide or oligosaccharide structure. Examples of substrates include glucose, dextrose, sucrose, fructose, mannose, lactose, starches such as hydrolyzed starch, maltodextrins and the like. The use of a glucose or a starch substrate is particularly preferred. The fermentation medium typically also contains organic nitrogen sources, phosphate salts which function to sequester calcium, more specifically alkali metal and ammonium phosphates as exemplified by dipotassium hydrogen phosphate and trace elements. An example of a typical fermentation using *Xanthomonas campestris* as the biologically active material is as follows, although as would be known by those skilled in the art, like procedures could be used to ferment the other above-mentioned bacteria.

As described in U.S. Pat. No. 3,516,983 and 4,135,979, Xanthomonas hydrophilic colloid can be biosynthesized by whole culture *Xanthomonas campestris* fermentation of a medium containing 2–5 percent of commercial glucose, an organic nitrogen source, dipotassium hydrogen phosphate, and appropriate trace elements.

The incubation time of the final medium is approximately 96 hours at 30° C. under aerobic conditions. In preparing the colloid, it is convenient to use corn steep liquor or distillers' dry solubles as an organic nitrogen source. It is convenient to grow the culture in two intermediate stages prior to the final inoculation in order to encourage vigorous growth of the bacteria. These stages may be carried out in media having a pH of about 7.

In the first stage a transfer from an agar slant to a dilute glucose broth may be made and the bacteria cultured for 24 hours under vigorous agitation and aeration at a temperature of about 30° C. The culture so produced may then be used to inoculate a higher glucose (3%) content broth of larger volume in a second intermediate stage. In this stage the reaction may be permitted to continue for 24 hours under the same conditions as the first stage. The culture so acclimated for use with glucose by the first and second stages is then added to the final glucose medium. In the said method of preparing *Xanthomonas campestris* hydrophilic colloid, a loopful of organism from the agar slant is adequate for the first stage comprising 290 milliliters of the glucose medium. In the second stage, the material resulting from the first stage may be used together with 9 times its volume of 3 percent glucose medium.

In the final stage the material produced in the second stage may be admixed with 19 times its volume of the final medium. A good final medium may contain 3 percent glucose, 0.5 percent distillers' solubles, 0.5 percent dipotassium phosphate, 0.1 percent magnesium sulfate having 7 molecules of water of crystallization, and water. The reaction in the final stage may be satisfactorily carried out for 96 hours at 30° C. with vigorous agitation and aeration.

The resultant raw Xanthomonas hydrophilic colloid fermentation liquor is referred to as a fermentation beer or a fermentation broth. A typical raw fermentation broth contains between about 0.5 to about 8.0, more preferably between about 3.0 to about 5.0 weight percent of dissolved Xanthomonas hydrophilic colloid, and has a viscosity in the range between about 500–100,000 cps at room temperature.

The broth is then subject to heat treatment for a time period and at a temperature suitable to deactivate the Xanthomonas organism. In prior art systems where the xanthan gum is ultimately recovered as a powder, both heat and isopropyl alcohol are used. In the present invention, no isopropyl alcohol is added.

The fermentation process of the present invention may also involve the addition of preservative agents after fermentation. The use of such preservatives is preferred as they function to extend the shelf life of the resulting broth, which is directly added into foodstuffs and/or pharmaceuticals. Any food grade preservative may be selected but included amongst preferred materials are sodium benzoate and acidic materials such as acetic acid, which is most preferred. The amount of preservative added can range from about 0.1 to about 20% by weight of the broth, with amounts ranging from about 0.5% to about 10% being more preferred.

The fermentation product broth will typically contain between about 0.5% to about 10.0% of the preservative material.

The broth can contain other optional additive materials depending on the final desired use. For example, bactericides, pH adjusting chemicals, dyes and colorants, spices, surface active agents, thickeners, texturizers, salts, flavors, are examples of such additives.

For use in liquid foodstuffs or pharmaceuticals, the liquid fermentation broth, optionally treated with a preservative, can directly be added into liquid medium. It is a simple mathematical calculation to determine how much of the broth should be added to the foodstuff or pharmaceutical. Simple analytical techniques can be used to determine the amount of the polysaccharide polymer in the broth. Using weight and volume analysis as would be well understood in the art would enable the practitioner to determine the equivalent volume of broth corresponding to a solid additive amount. For example, a formulation requiring 0.5 percent by weight of xanthan gum (solid) would require the addition of 12.5 parts of a xanthan broth having a concentration of 4% xanthan gum.

The fermentation broth can be used with any liquid foodstuff or pharmaceutical which would benefit from having the fermentation polymer in its formulation. In most applications, this would involve the use of the polymer as a viscosity agent, such as the use of xanthan gum as a thickening agent. Examples of the types of foods or pharmaceuticals in which the broth could be utilized include, but are not limited to the following classes of materials: salad dressings, sauces, soups, syrups, condiments, gravies, bakery goods, bakery fillings, puddings, gelatin desserts, beverages, milkshakes, frozen foods and pharmaceutical suspensions. In practice, the amount of broth added to such foods or pharmaceuticals is an amount so that the amount of active biopolymer ranges between about 0.01 to about 2.0 percent by weight of the final product, more preferably between about 0.1 to about 1.0 percent by weight of the final product.

It has been surprisingly discovered that the use of the inventive polymer broth can provide better viscosity performance in homogenized foods such as salad dressings. As will be demonstrated in the examples, when conducting direct comparisons between homogenized liquid foods, the use of a xanthan fermentation broth provides better viscosity performance as compared to the conventional addition of xanthan gum, namely addition in a powdered, purified form. In addition, because the biopolymer is already present in an aqueous environment, improved dispersibility results from using the broth directly into final formulated foods or pharmaceuticals.

The invention is described in greater detail by the following non-limiting examples.

EXAMPLE 1

Production of Liquid Fermentation Broth Product

For this synthesis the generally understood method for producing a xanthan gum fermentation broth is utilized (such as the methods as illustrated in prior art such as U.S. Pat. Nos. 3,000,790; 3,020,207; 3,557,016 or 4,299,825). More specifically, a xanthan gum fermentation broth is prepared under biosynthesis conditions by fermentation of the microorganism *Xanthomonas campestris* operating on a substrate of hydrolyzed potato starch or equivalent sugar. After fermentation, the broth is heated to 120° C. for 20 minutes without removal of substantially any liquid in order to deactivate the Xanthomonas organism and glacial acetic acid in an amount of about 10 percent by weight of the resulting broth is added to the broth as a preservative in an amount so that the pH of the broth is lowered to 3.0. The percentage of xanthan gum present in the broth is 3.24% by weight of the broth. No post-fermentation concentrating, precipitating, drying, sieving or grinding steps were conducted in connection with the obtention of the liquid fermentation broth product of this Example containing xanthan hydrocolloid.

COMPARATIVE EXAMPLE 2

Production of Xanthan Gum Powder

The typical post-fermentation processing steps are performed on the fermentation broth obtained after completion of the fermentation step in Example 1 and without the heating and addition of glacial acetic acid described in Example 1. More specifically, the xanthan gum broth is heated, added to isopropanol, precipitated, centrifuged and dried to remove most of the liquid and milled and sieved to yield a powder. The moisture content of the resulting powder is 9.8%, which is within the normal 6 to 12% moisture level specification for such a powder product.

EXAMPLE 3

Hydration Properties of Example 1 and Comparative Example 2 Compositions

Two aqueous solutions are prepared for purposes of measuring hydration properties of the Example 1 and Comparative Example 2 compositions. The amounts are added so that each aqueous solution contains 0.5% by weight of xanthan gum. The solutions are as follows. All parts are listed by weight.

| Solution A | |
|---|---|
| Component | Amount (by weight) |
| Example 1 Composition | 17.089 |
| Tripotassium Phosphate (1M) | 15.190 |
| Sodium Hydroxide (10N) | 1.510 |
| Distilled Water | 66.211 |
| TOTAL | 100.00 |

| Solution B | | |
|---|---|---|
| Component | Amount (by weight) | |
| Comp. Ex. 2 Composition | 0.5500 | |
| Tripotassium Phosphate (1M) | 15 | 190 |
| Sodium Hydroxide (10N) | 1.5100 | |

-continued

Solution B

| Component | Amount (by weight) |
| --- | --- |
| Distilled Water | 81.0411 |
| Glacial Acetic Acid | 1.7089 |
| TOTAL | 100.00 |

To determine the hydration properties of the respective solutions, the following test procedures are utilized.

Waring Blender Method:

Solution A:

In a mixer bowl, weigh an aqueous solution containing the tripotassium phosphate and sodium hydroxide and add pre-weighed liquid xanthan broth and turn on the mixer and increase the speed to 2000 rpm and mix for five minutes at 2000 rpm. After five minutes of mixing, the bowl is removed and the solution is poured into a 600 ml beaker. Using a Brookfield LV Viscometer, Spindle #3 or 4, 60 rpm a viscosity reading is taken. Measurements are taken every fifteen minutes thereafter until 60 minutes after initial agitation.

Solution B:

In a mixer bowl weigh the water, turn on the mixer and increase speed to 2000 rpm. Sprinkle the gum into the vortex of the mixer and add over a one-minute period. After five minutes of mixing, the glacial acetic acid, sodium hydroxide and tripotassium phosphate are added and mixing continues until the mixture is uniform in consistency. The bowl is removed and the solution is poured into a 600 ml beaker. Using a Brookfield LV Viscometer, Spindle #3 or 4, 60 rpm a viscosity reading is taken. Measurements are taken every fifteen minutes thereafter until 60 minutes after initial agitation.

The viscosity profile for each of the Solutions is as follows. Measurements are in cps.:

| Time | Solution A | Solution B |
| --- | --- | --- |
| Initial | 770 | 730 |
| 15 minutes | 810 | 770 |
| 30 minutes | 800 | 830 |
| 60 minutes | 800 | 800 |

The above data demonstrates that the respective materials behave nearly identical in their hydration in water.

EXAMPLE 4

Salad Dressing Composition using Example 1 Composition

To produce a low fat (8% fat) Italian-type salad dressing using the liquid xanthan fermentation broth product of Example 1, the following procedure is used. 6.00 parts of sucrose are added to 55.90 parts of water and the solution is mixed at 500 rpm for two minutes. 27.40 parts of the Example 1 Composition are slurried in 8.20 parts of soybean oil and this slurry is added to the water/sucrose solution and is mixed at 2000 rpm for 3 minutes. 2.50 parts of sodium chloride are added to the solution and the mixture is mixed at 2000 rpm for 3 minutes.

The mixture is split into two parts for comparative testing purposes. The first part is set aside for viscosity measurements and is referred to as Example 4A. The other part is continuously homogenized at 2500 pounds per square inch using a Microfluidics Homogenizer (HC-5000) and is then cooled to 25° C. and is referred to as Example 4B. Viscosity measurements are taken on this part. Homogenization is performed in order to break down the fat present in the mixture to form a stable suspension.

Figure 2:
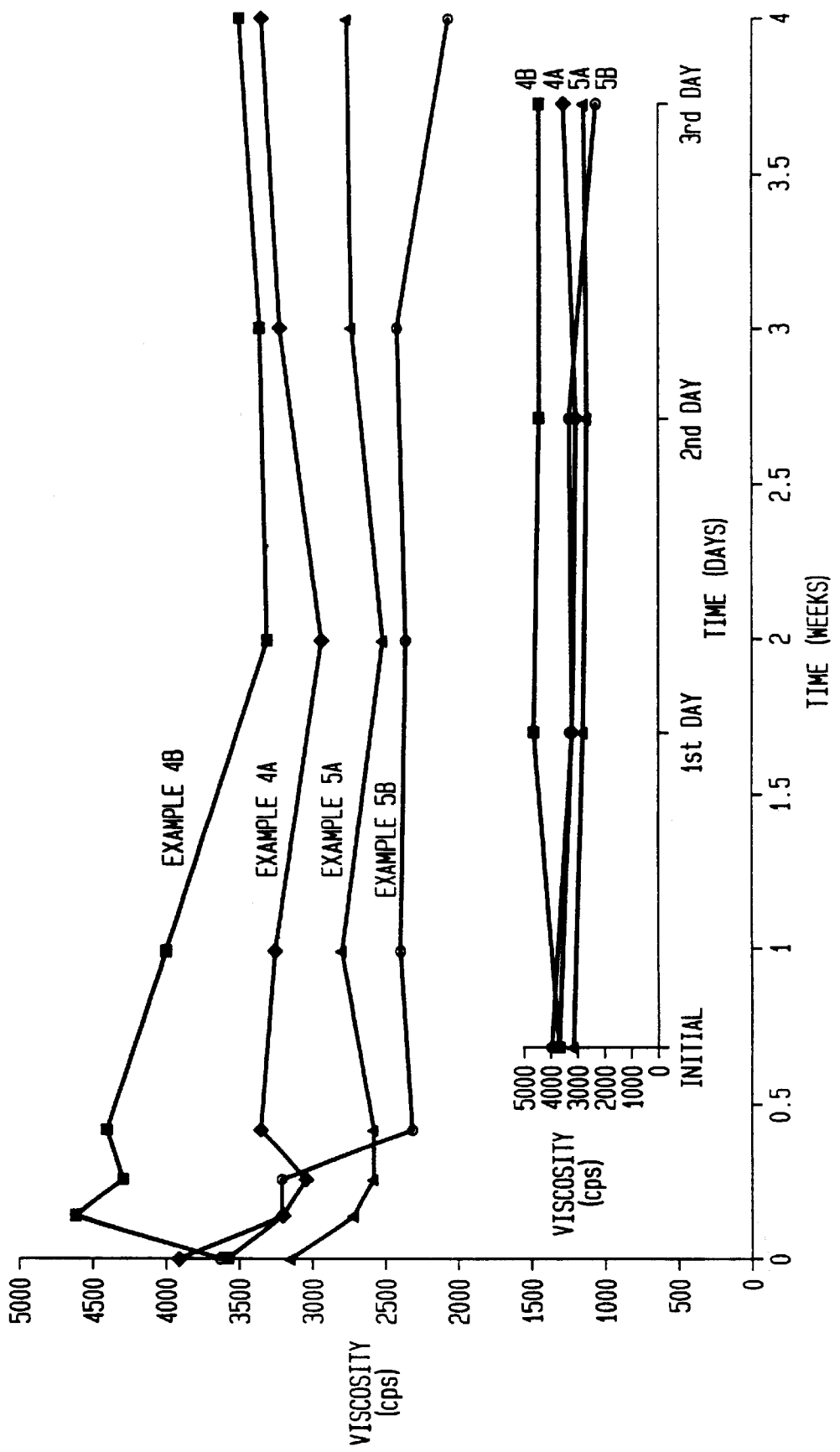

All measurements are taken using a Brookfield LVT Viscometer using Spindle #3 or 4, at either 12 or 60 rpm. Measurements are taken at intervals of one, two, three days, one week, two weeks, three weeks and four week intervals. The results are shown in FIGS. 1 and 2.

EXAMPLE 5

Salad Dressing Composition using Comparative Example 2 Composition

To produce a low fat (8% fat) Italian-type salad dressing using the xanthan powder of Comparative Example 2, the following procedure is used. 6.00 parts of sucrose are added to 64.57 parts of water and the solution is mixed at 500 rpm for two minutes. 0.89 parts of the Comparative Example 2 Composition are slurried in 8.20 parts of soybean oil and this slurry is added to the water/sucrose solution and is mixed at 2000 rpm for 3 minutes. 2.50 parts of sodium chloride, 17.20 parts of vinegar (120 grain) and 0.64 parts of glacial acetic acid are added to the solution and the mixture is mixed at 2000 rpm for 3 minutes. The acetic acid and vinegar are added to compensate for the acetic acid already present in the Example 1 Composition so that a like comparison can be made.

The mixture is split into two parts for comparative testing purposes. The first part is set aside for viscosity measurements and is referred to as Example 5A. The other part is continually homogenized at 2500 pounds per square inch using a Microfluidics Homogenizer (HC-5000) and is then cooled to 25° C. and is referred to as Example 5B. Viscosity measurements are taken on this part. Homogenization is performed in order to break down the fat present in the mixture to form a stable suspension.

All measurements are taken using a Brookfield LVT Viscometer at Spindle #3 or 4, at either 12 or 60 rpm. Measurements are taken at intervals of one, two, three days, one week, two weeks, three weeks and four weeks. The results are shown in FIGS. 1 and 2.

As is seen in FIGS. 1 and 2, the compositions made from the liquid xanthan gum demonstrate superior hydration performance as compared to those made from powdered xanthan gum. In fact, for the homogenized samples, the hydration performance of the composition containing liquid xanthan gum (4B) is unexpectedly superior to that of the composition containing powder xanthan (5B). As is seen in the Figures, Example 4B initially shows a dramatic increase in viscosity after one day as compared to Example 5B, which loses a significant amount of viscosity. The viscosity of Example 4B actually shows an increase over the time period of two weeks to four weeks, whereas the viscosity of Example 5B either stays approximately the same or decreases.

Accordingly, in addition to the tremendous processing cost savings associated with using a liquid fermentation broth directly into liquid foodstuffs or pharmaceuticals, the above data demonstrates unexpectedly good results when using the liquid fermentation product inprocessed foods, and particularly homogenized foods. In addition, because the biopolymer is already present in an aqueous environment, it has improved dispersibility features as compared to solid powders used as rheology/thickening agents.

EXAMPLE 6

Figure 3:
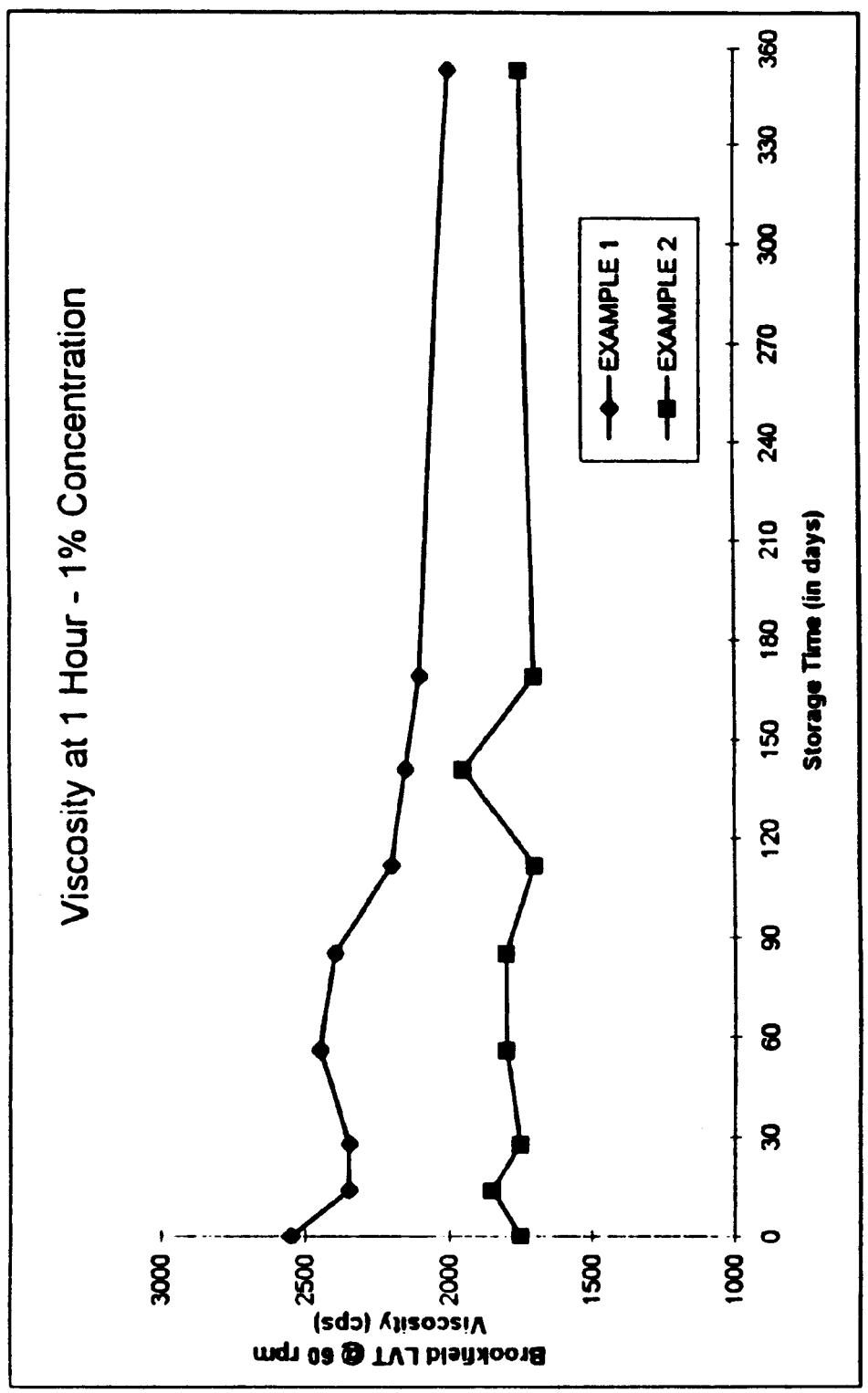
FIG. 3 is a viscosity graph for ambient stability of the Composition of Example 1.

The liquid fermentation broth product of Example 1 and the xanthan gum product of Comparative Example 2 were allowed to stand over a period of 353 days. Periodically, during the 353 day period, they were each formulated as uniformly mixed aqueous solutions containing 1% xanthan gum. The solutions were, tested for stability by measuring the viscosity thereof, one hour after mixing, using a Brookfield LV Viscometer, Spindle #3 or 4, at 60 rpm. The ambient viscosity data for the formulations from Example 1 and Comparative Example 2 is set forth in FIG. 3. The ambient viscosity data in FIG. 3 clearly shows the Example 1 formulation is stable at ambient temperature for 353 days, and has a higher viscosity than the viscosity of the formulation from Comparative Example 2 due to the greater ionic strength of the liquid fermentation broth compared to the ionic strength of the Comparative Example 2 solution.

The microbiological stability of the liquid fermentation broth product of Example 1 was also monitored for 353 days at ambient temperature by testing the broth product for growth of aerobic plate count (APC), yeast and mold on typical media used for such analyses. The microbiological stability data is set forth in the following Table and clearly shows the microbiological stability over the 353 day period.

TABLE

Microbial Study

|  | APC Col/g | Yeast Col/g | Mold Col/g |
| --- | --- | --- | --- |
| 0 Days | 100 | <100 | <100 |
| 14 Days | 200 | <100 | <100 |
| 28 Days | <100 | <100 | <100 |
| 56 Days | <100 | <100 | <100 |
| 85 Days | <100 | <100 | <100 |
| 112 Days | <100 | <100 | <100 |
| 141 Days | <100 | <100 | <100 |
| 169 Days | <100 | <100 | <100 |
| 353 Days | <100 | <100 | <100 |

Having described the invention in detail and by reference to the preferred embodiments thereof, it will be apparent that modifications and variations are possible without departing from the scope of the appended claims.

What is claimed is:

1. A method for making a food or pharmaceutical composition comprising the steps of:

(a) fermenting a Xanthomonas bacterium in a carbohydrate medium other than dairy whey to yield a liquid fermentation broth product which is a hydrocolloid-containing thickening agent for the composition; and (b) directly adding, without any concentrating, drying, or precipitation steps, said liquid fermentation broth product to a food or pharmaceutical ingredient as a thickening agent to yield the food or pharmaceutical composition.

2. The method according to claim 1 wherein said liquid fermentation broth product comprises xanthan gum.

3. The method according to claim 1 comprising the additional step of homogenizing said food or pharmaceutical composition after addition of the liquid fermentation broth product.

4. The method according to claim 1 wherein said carbohydrate medium is selected from the group consisting of glucose, dextrose, sucrose, fructose, mannose, lactose, oligosaccharides, starches, maltodextrins and mixtures thereof.

5. The method according to claim 4 wherein said carbohydrate medium comprises glucose or hydrolyzed starch.

6. The method according to claim 1 wherein said liquid fermentation product further comprises one or more preservatives.

7. The method according to claim 6 wherein said preservative comprises acetic acid.

* * * * *